(12) United States Patent
Umeda et al.

(10) Patent No.: US 6,709,398 B2
(45) Date of Patent: Mar. 23, 2004

(54) ULTRASONIC PROBE

(75) Inventors: Manabu Umeda, Tokyo (JP); Mitsuhiro Nozaki, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/302,138

(22) Filed: Nov. 22, 2002

(65) Prior Publication Data

US 2003/0100834 A1 May 29, 2003

(30) Foreign Application Priority Data

Nov. 26, 2001 (JP) .......................... 2001-359945

(51) Int. Cl.[7] ................................ A61B 8/14
(52) U.S. Cl. ............................................. 600/459
(58) Field of Search ................... 600/407–471; 367/7, 11, 130, 138; 73/625, 626; 128/916

(56) References Cited

U.S. PATENT DOCUMENTS

| | | |
|---|---|---|
| 5,042,493 A | 8/1991 | Saito et al. |
| 5,115,809 A | 5/1992 | Saitoh et al. |
| 5,176,140 A | 1/1993 | Kami et al. |
| 5,274,296 A | 12/1993 | Hiki et al. |
| 5,295,487 A | 3/1994 | Saitoh et al. |
| 5,398,689 A | 3/1995 | Connor et al. |
| 5,810,009 A | 9/1998 | Mine et al. |
| 5,810,733 A * | 9/1998 | Van Creveld et al. ...... 600/459 |
| 6,020,675 A | 2/2000 | Yamashita et al. |

* cited by examiner

*Primary Examiner*—Ali M. Imam
(74) *Attorney, Agent, or Firm*—Carl B. Horton, Esq.; Armstrong Teasdale LLP

(57) ABSTRACT

For the purpose of reducing the numbers of members and molds to reduce the cost of manufacture, and improving grippability in an ultrasonic probe, a fixing member 6 fitted with an ultrasonic element 3, a broad cable 4, a connector 5, and a connection cable 2 is inserted into a mold, and an ultrasonic lens portion 11, a case 12, and a bushing portion 13 are integrally molded by insert molding. Since an ultrasonic probe 10 is made using a single mold, the number of members is reduced, the number of assembly steps is reduced, and reduction in the cost of manufacture can thus be achieved.

5 Claims, 16 Drawing Sheets

ULTRASONIC PROBE

CROSS REFERENCE TO RELATED APPLICATIONS

This application claims the benefit of Japanese Application No. 2001-359945 filed Nov. 26, 2001.

BACKGROUND OF THE INVENTION

The present invention relates to an ultrasonic probe for imaging a subject with reflection of ultrasound, and more particularly to an ultrasonic probe in which the cost of manufacture is reduced and grippability is improved.

Conventionally, an ultrasonic imaging apparatus for imaging the interior of a subject by illuminating the subject with ultrasound and producing an image of reflection waves of the ultrasound has been commonly used in non-destructive inspection. Since ultrasound is harmless to living bodies, the ultrasonic imaging apparatus is especially useful for medical purposes, and used in detection of a foreign material within a living body, determination of the degree of lesion, observation of tumors, and observation of a fetus, for example.

When local information on a subject is to be acquired with ultrasound, an ultrasonic probe that is gripped by an operator and is capable of abutting against a desired portion of the subject is generally used. FIG. 15 is a perspective view showing the general configuration of a conventional ultrasonic probe. FIG. 16 is an exploded view of the ultrasonic probe shown in FIG. 15. In FIGS. 15 and 16, the ultrasonic probe 100 comprises an ultrasonic element 3 at the tip portion of a case 102 made of a hard resin. The case 102 is formed by combining a case member 102a and a case member 102b, and is provided with an opening portion near the ultrasonic element 3 for fitting an ultrasonic lens 101 therein.

A broad cable 4 connected with the ultrasonic element 3 is connected to a connection cable 2 via a connector 5, and the connection cable 2 is connected to an ultrasonic imaging apparatus (not shown). A pass-through portion through which the connection cable 2 passes into the case 102 is provided with a bushing portion 103. The bushing portion 103 is made of a material such as a rubber, and serves as a cable protection portion for preventing breakage of the connection cable 2 by limiting flexure of the connection cable 102 at the pass-through portion. The case 102 is also provided with a grip portion 104 that can be gripped by the operator, and the grip portion 104 is provided with a plurality of concave portions 105 for preventing slipping.

The ultrasonic element 3 is supplied with electric power from the broad cable 4, and generates ultrasound. The generated ultrasound is focused by the ultrasonic lens portion 101, and the subject to be imaged is illuminated with the focused ultrasound. The ultrasonic element 3 also receives reflection waves that are ultrasound reflected by the subject to be imaged, converts the received waves into electric signals, and outputs them to the broad cable 4. The broad cable 4 transmits the electric signals output by the ultrasonic element 3 to the ultrasonic imaging apparatus (not shown) via the connector 5 and connection cable 2. The ultrasonic imaging apparatus produces an image of the imaged subject based on the electric signals received from the connection cable 2.

In performing imaging, the operator grips the grip portion 104 and puts the ultrasonic lens portion 101 against a desired portion in the subject to be imaged to conduct imaging. At that time, a solvent for ultrasonic examination is usually applied to the subject to be imaged. The solvent for ultrasonic examination is a gel-type solvent that has an acoustic impedance similar to that of the human body and prevents attenuation of ultrasound. By applying such a solvent, multiple reflection can be suppressed and noise can be prevented. The tip portion of the ultrasonic probe 100 may be inserted into a body cavity, i.e., into the esophagus, intestine, vagina, anus or the like, to acquire information on the interior of the living body.

However, the conventional ultrasonic probe as described above is an assembly formed of the case members 102a and 102b, ultrasonic lens portion 101, and bushing portion 103, and therefore, it is necessary to prepare a mold for each member, and steps of making the members separately, assembling them, and bonding them together are needed. This leads to a problem of high cost of manufacture.

Moreover, since the case 102 is made of a hard resin, the case 102 is likely to slip when employed, and this leads to problems that there is a possibility of breakage by dropping, and ultrasound cannot be stably focused.

SUMMARY OF THE INVENTION

Therefore, the object of the present invention is to provide an ultrasonic probe in which the numbers of members and molds are reduced to lower the cost of manufacture, and grippability is improved.

The present invention, in accordance with a first aspect for solving the aforementioned problems and attaining the object, is an ultrasonic probe having an ultrasonic element for emitting ultrasound and converting reflection waves of said ultrasound into electric signals, and a cable for supplying electric power to said ultrasonic element and transmitting said electric signals, said ultrasonic probe characterized in comprising: a case for accommodating said ultrasonic element, and provided with a grip portion that can be gripped by an operator; a cable protection portion provided at a pass-through portion of said cable for limiting flexure of said cable; and an ultrasonic lens for focusing said ultrasound, wherein said case, said ultrasonic lens, and said cable protection portion are formed by integral molding.

According to the invention of the first aspect, since the case, ultrasonic lens and cable protection portion of the ultrasonic probe are formed by integral molding of a single material, the number of necessary molds is reduced, and grippability is improved.

The present invention in accordance with a second aspect is an ultrasonic probe having an ultrasonic element for emitting ultrasound and converting reflection waves of said ultrasound into electric signals, and a cable for supplying electric power to said ultrasonic element and transmitting said electric signals, said ultrasonic probe characterized in comprising: a case for accommodating said ultrasonic element, and provided with a grip portion that can be gripped by an operator; a cable protection portion provided at a pass-through portion of said cable for limiting flexure of said cable; and an ultrasonic lens for focusing said ultrasound, wherein said ultrasonic lens and said cable protection portion are formed by integral molding.

According to the invention of the second aspect, since the ultrasonic lens and cable protection portion are formed by integral molding of a single material, the number of necessary molds is reduced.

The present invention in accordance with a third aspect is characterized in that, in the invention of the second aspect, said case is formed on the surface of said ultrasonic lens and said cable protection portion that are formed by said integral molding.

According to the invention of the third aspect, since the case is formed on the surface of the ultrasonic lens and cable retaining portion formed by integral molding, the number of necessary molds is reduced, and the strength of the ultrasonic probe is improved.

The present invention in accordance with a fourth aspect is an ultrasonic probe having an ultrasonic element for emitting ultrasound and converting reflection waves of said ultrasound into electric signals, and a cable for supplying electric power to said ultrasonic element and transmitting said electric signals, said ultrasonic probe characterized in comprising: a case for accommodating said ultrasonic element, and provided with a grip portion that can be gripped by an operator; and an ultrasonic lens for focusing said ultrasound, wherein said ultrasonic lens and said case are formed by integral molding.

According to the invention of the fourth aspect, since the case and ultrasonic lens of the ultrasonic probe are formed by integral molding of a single material, the number of necessary molds is reduced, and grippability is improved.

The present invention in accordance with a fifth aspect is an ultrasonic probe having an ultrasonic element for emitting ultrasound and converting reflection waves of said ultrasound into electric signals, and a cable for supplying electric power to said ultrasonic element and transmitting said electric signals, said ultrasonic probe characterized in comprising: a case for accommodating said ultrasonic element, and provided with a grip portion that can be gripped by an operator; and a cable protection portion provided at a pass-through portion of said cable for limiting flexure of said cable, wherein said case and said cable protection portion are formed by integral molding.

According to the invention of the fifth aspect, since the case and cable protection portion of the ultrasonic probe are formed by integral molding of a single material, the number of necessary molds is reduced, and grippability is improved.

The present invention in accordance with a sixth aspect is an ultrasonic probe having an ultrasonic element for emitting ultrasound and converting reflection waves of said ultrasound into electric signals, and a cable for supplying electric power to said ultrasonic element and transmitting said electric signals, said ultrasonic probe characterized in comprising: a case for accommodating said ultrasonic element, and provided with a grip portion that can be gripped by an operator; a cable protection portion provided at a pass-through portion of said cable for limiting flexure of said cable; and an ultrasonic lens for focusing said ultrasound, wherein said cable protection portion covers at least said grip portion.

According to the invention of the sixth aspect, since the cable protection portion that covers the grip portion of the ultrasonic probe is provided, grippability during operation is improved.

The present invention in accordance with a seventh aspect is characterized in that, in the invention of the sixth aspect, said cable protection portion and said case are formed by two-color molding employing a common mold.

According to the invention of the seventh aspect, since the case of the ultrasonic probe is formed with the cable protection portion using two-color molding, and the grip portion of the ultrasonic probe is covered with the cable protection portion, the number of molds and the number of steps are reduced, and grippability during operation is improved.

The present invention in accordance with an eighth aspect is characterized in that, in the invention of the first—seventh aspects, said ultrasonic probe further comprises a fixing member for fixing said ultrasonic element, wherein said case, said ultrasonic lens, and said cable protection portion are formed on the surface of said fixing member.

According to the invention of the eighth aspect, since the case, ultrasonic lens and cable protection portion are formed on the surface of a fixing member fitted with the ultrasonic element, the ultrasonic probe can be made by insert molding.

The present invention in accordance with a ninth aspect is characterized in that, in the invention of the eighth aspect, said fixing member has a positioning portion for positioning said ultrasonic element, and said positioning portion determines the positional relationship between said ultrasonic element and said ultrasonic lens portion.

According to the invention of the ninth aspect, since the positional relationship between the ultrasonic element and ultrasonic lens portion is determined by a positioning portion provided in the fixing member, the characteristics of the ultrasonic lens portion can be defined with high precision.

Further objects and advantages of the present invention will be apparent from the following description of the preferred embodiments of the invention as illustrated in the accompanying drawings.

DETAILED DESCRIPTION OF THE INVENTION

An ultrasonic probe in accordance with several embodiments of the present invention will now be described in detail with reference to the accompanying drawings.

Embodiment 1.

Figure 2:
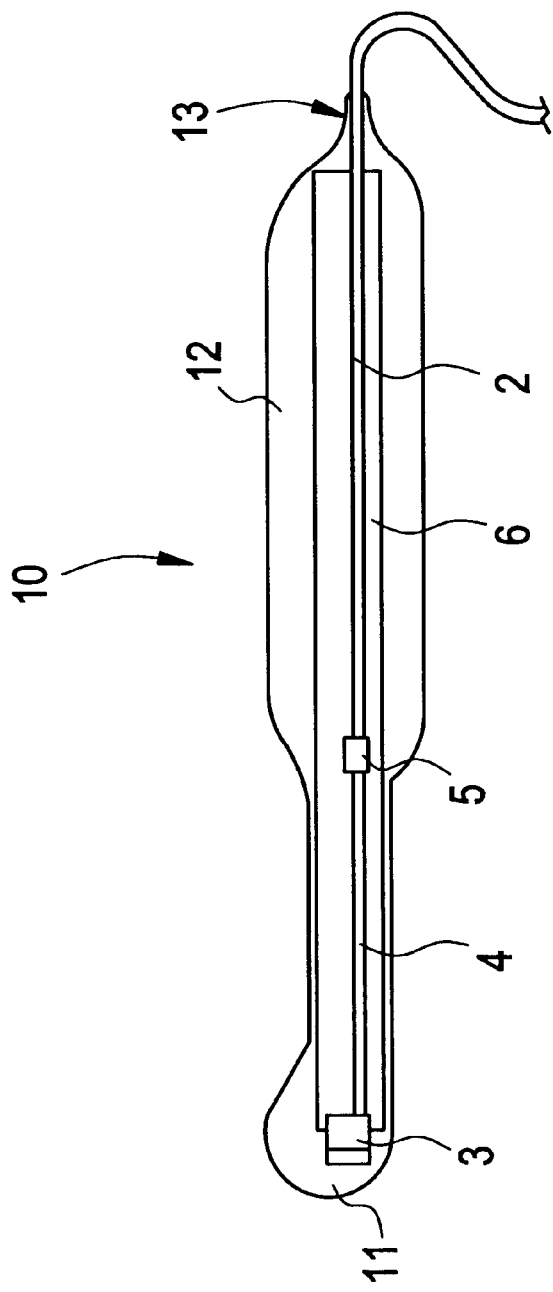
FIG. 2 is a cross-sectional view of the ultrasonic probe 10 shown in FIG. 1 taken along line A—A.
Figure 3:
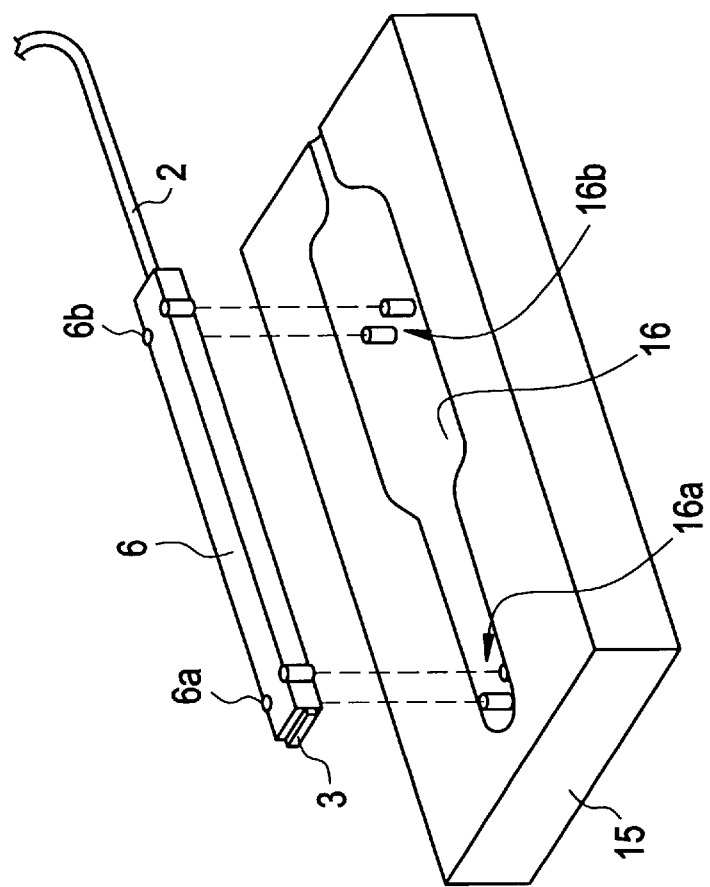
FIG. 3 shows a method of disposing a fixing member 6 when a mold and a fixing member 6 are provided with a positioning portion.

In Embodiment 1, an ultrasonic probe 10 made by integral molding of a case, an ultrasonic lens portion, and a bushing portion will be described with reference to FIGS. 1–3. This ultrasonic probe 10 has a configuration such that the probe 10 has a tip portion intended for insertion into the body cavity and an ultrasonic element is fitted in the tip portion.

Figure 1:
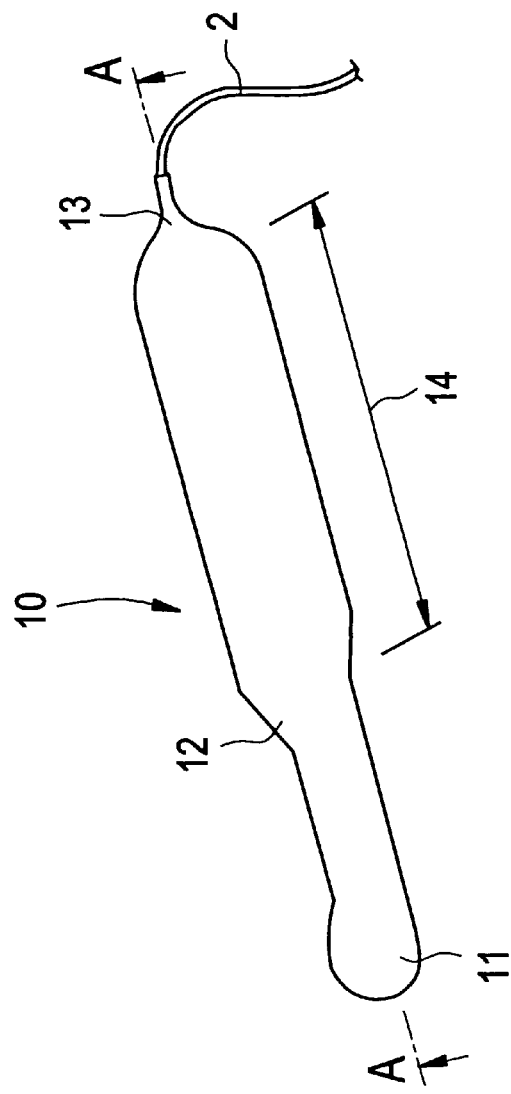
FIG. 1 is a perspective view showing the general configuration of an ultrasonic probe in accordance with Embodiment 1.

FIG. 1 is a perspective view showing the general configuration of the ultrasonic probe in accordance with Embodiment 1. FIG. 2 is a cross-sectional view of the ultrasonic probe 10 shown in FIG. 1 taken along line A—A. In FIGS. 1 and 2, the ultrasonic probe 10 has therein an ultrasonic element 3, a broad cable 4, a connector 5, and a fixing member 6. The ultrasonic element 3 is fitted in the fixing member 6, and disposed near the tip portion of the case 12. The broad cable 4 connected with the ultrasonic element 3 is connected to a connection cable 2 via the connector 5, and the connection cable 2 is connected to an ultrasonic imaging apparatus (not shown). It should be noted that the broad cable 4, connector 5 and connection cable 2 are fitted in the fixing member 6 and are fixed.

The case 12 forms an ultrasonic lens portion 11 near the ultrasonic element 3. The case 12 also forms a bushing portion 13 at a pass-through portion through which the connection cable 2 passes into the case 12. The bushing portion 13 serves as a cable protection portion for preventing breakage of the connection cable 2 by limiting flexure of the connection cable 2 at the pass-through portion. Moreover, the case 12 comprises a grip portion 14 that can be gripped by an operator.

The ultrasonic element 3 is supplied with electric power from the broad cable 4, and generates ultrasound. The generated ultrasound is focused by the ultrasonic lens portion 11, and the subject to be imaged is illuminated with the focused ultrasound. The ultrasonic element 3 also receives reflection waves that are ultrasound reflected by the subject to be imaged, converts the received waves into electric signals, and outputs them to the broad cable 4. The broad cable 4 transmits the electric signals output by the ultrasonic element 3 to the ultrasonic imaging apparatus (not shown) via the connector 5 and connection cable 2. The ultrasonic imaging apparatus produces an image of the imaged subject based on the electric signals received from the connection cable 2.

In performing imaging, the operator grips the grip portion 14 and puts the ultrasonic lens portion 11 against a desired portion in the subject to be imaged to conduct imaging. At that time, a solvent for ultrasonic examination may be applied to the subject to be imaged. The solvent for ultrasonic examination is a gel-type solvent that has an acoustic impedance similar to that of the human body and prevents attenuation of ultrasound. By applying such a solvent, multiple reflection can be suppressed and noise can be prevented. The tip portion of the ultrasonic probe 10 may be inserted into a body cavity, i.e., into the esophagus, intestine, vagina, anus or the like, to acquire information on the interior of the living body.

In making the ultrasonic probe 10, the ultrasonic element 3, broad cable 4, connector 5, and connection cable are first fitted in the fixing member 6. The fixing member 6 is next positioned in the interior of a mold having a cavity corresponding to the case 12. By injecting into the cavity a silicon resin that will serve as the ultrasonic lens, the case 12 can be integrally molded, and the ultrasonic lens portion 11 and bushing portion 13 can be formed at the same time.

A method of disposing the fixing member 6 in the interior of the mold can be arbitrarily selected for use from among, for example, a method involving suspending the fixing member 6 within the cavity using the connection cable 2, and a method involving providing the mold and fixing member 6 with a positioning portion for positioning. FIG. 3 shows a method of disposing the fixing member 6 when the mold and fixing member 6 are provided with the positioning portion. In FIG. 3, a lower mold 15 has a cavity 16, and the cavity 16 is provided in the inside thereof with positioning pins 16a and 16b. The fixing member 6 has a positioning portion 6a corresponding to the positioning pin 16a and a positioning portion 6b corresponding to the positioning pin 16b.

When the fixing member 6 is disposed in the lower mold 15, the positional relationship between the mold 15 and the fixing member 6 can be determined by inserting the positioning pin 16a into the positioning portion 6a and the positioning pin 16b into the positioning portion 6b. In the ultrasonic probe 10, since the ultrasonic lens portion 11 is formed simultaneously with the case 12 by integral molding of the case 12, the positional relationship between the mold 15 and the fixing member 6 determines the positional relationship of the ultrasonic element 3 and ultrasonic lens portion 11, thus affecting the characteristics of the ultrasonic lens portion 11. Therefore, the characteristics of the ultrasonic lens portion 11 can be defined with high precision by disposing the positioning pin 16a and the positioning portion 6a near the ultrasonic lens portion 11.

As described above, since the ultrasonic lens portion 11 and the bushing portion 13 are formed simultaneously with the case 12 during integral molding of the case 12 in the ultrasonic probe 10 in accordance with Embodiment 1, the ultrasonic probe 10 can be made using a single mold. Thus, the number of members is reduced, the number of assembling steps is reduced, and reduction in the cost of manufacture can thus be achieved.

Moreover, since the ultrasonic lens portion 11, case 12, and bushing portion 13 are formed by integral molding of the silicon material that serves as the ultrasonic lens, the function as the cable protection portion is fully achieved in the bushing portion 13, and slipping is prevented and grippability is improved in the grip portion 14. Furthermore, by integral molding the case 12, gaps and seams are eliminated in the appearance of the ultrasonic probe 10, improving aesthetics.

While the connection cable 2 and the broad cable 4 are connected to each other via the connector 5 in this embodiment, a configuration in which the connection cable 2 is soldered directly to the broad cable 4 without the connector 5 is possible.

Embodiment 2.

An ultrasonic probe in accordance with Embodiment 2 will now be described. While the case 12, ultrasonic lens portion 11 and bushing portion 13 were formed by integral molding in the ultrasonic probe 10 in accordance with Embodiment 1 as described above, an ultrasonic probe 20 presented in Embodiment 2 has an ultrasonic lens portion and a case separately molded, and a bushing portion is molded covering part of the surface of the case. The remainder of the configuration is similar to the ultrasonic probe 10 described in Embodiment 1, and similar components are designated by like symbols.

Figure 4:
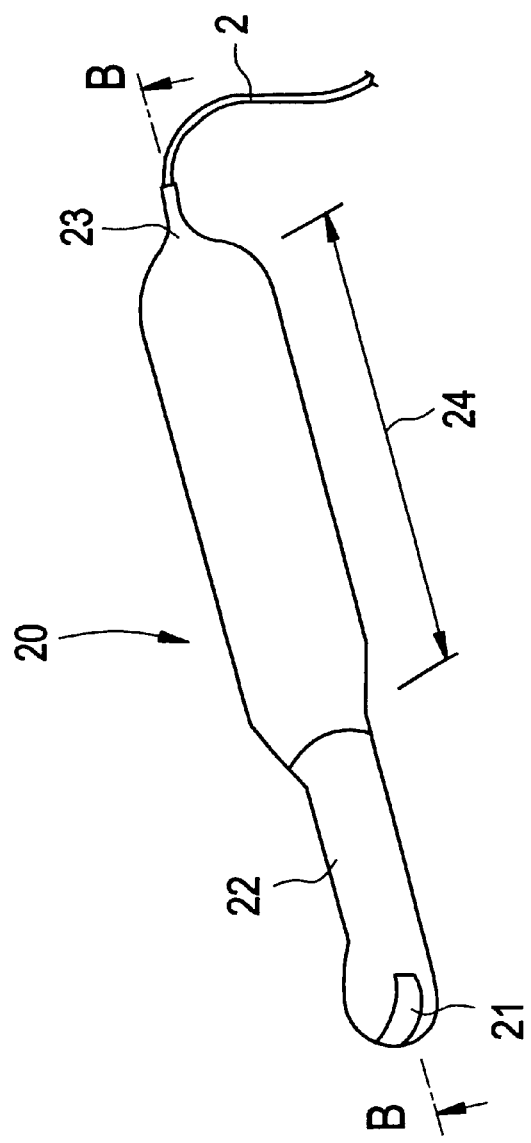
FIG. 4 is a perspective view showing the general configuration of an ultrasonic probe 20 that is Embodiment 2 of the present invention.
Figure 5:
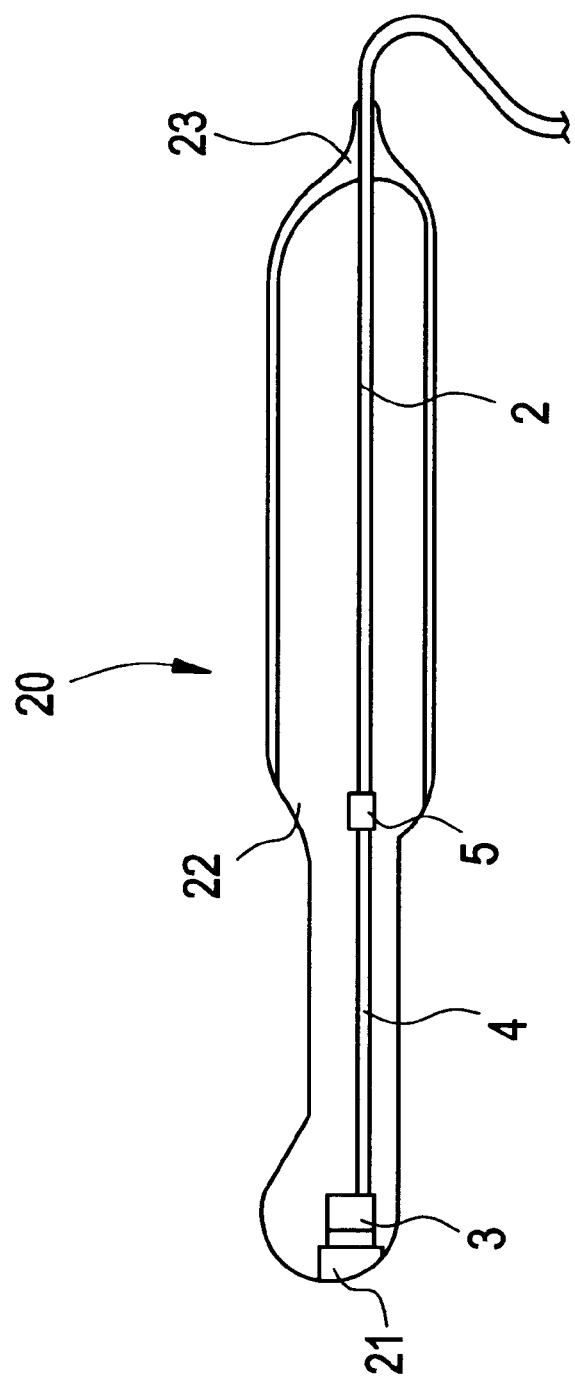
FIG. 5 is a cross-sectional view of the ultrasonic probe 20 shown in FIG. 4 taken along line B—B.

FIG. 4 is a perspective view showing the general configuration of the ultrasonic probe 20 that is Embodiment 2 of the present invention. FIG. 5 is a cross-sectional view of the ultrasonic probe 20 shown in FIG. 4 taken along line B—B. In FIGS. 4 and 5, the ultrasonic probe 20 has an ultrasonic element 3 at the tip portion of a case 22. A broad cable 4 connected with the ultrasonic element 3 is connected to a connection cable 2 via the connector 5, and the connection cable 2 is connected to an ultrasonic imaging apparatus (not shown).

The case 22 comprises a grip portion 24 that can be gripped by the operator. Moreover, the ultrasonic probe 20 comprises a bushing portion 23 at a pass-through portion through which the connection cable 2 passes into the case 22. The bushing portion 23 serves as a cable protection portion for preventing breakage of the connection cable 2 by limiting flexure of the connection cable 2 at the pass-through portion. The bushing portion 23 covers the grip portion 24, and serves as a slip stopper.

The ultrasonic element 3 is supplied with electric power from the broad cable 4, and generates ultrasound. The generated ultrasound is focused by an ultrasonic lens portion 21, and the subject to be imaged is illuminated with the focused ultrasound. The ultrasonic element 3 also receives reflection waves that are ultrasound reflected by the subject to be imaged, converts the received waves into electric signals, and outputs them to the broad cable 4. The broad cable 4 transmits the electric signals output by the ultrasonic element 3 to the ultrasonic imaging apparatus (not shown) via the connector 5 and connection cable 2. The ultrasonic imaging apparatus produces an image of the imaged subject based on the electric signals received from the connection cable 2.

In performing imaging, the operator grips the grip portion 24 and puts the ultrasonic lens portion 21 against a desired portion in the subject to be imaged to conduct imaging. At that time, a solvent for ultrasonic examination may be applied to the subject to be imaged. The tip portion of the ultrasonic probe 20 may be inserted into the body cavity, i.e., into the esophagus, intestine, vagina, anus or the like, to acquire information on the interior of the living body.

Figure 6:
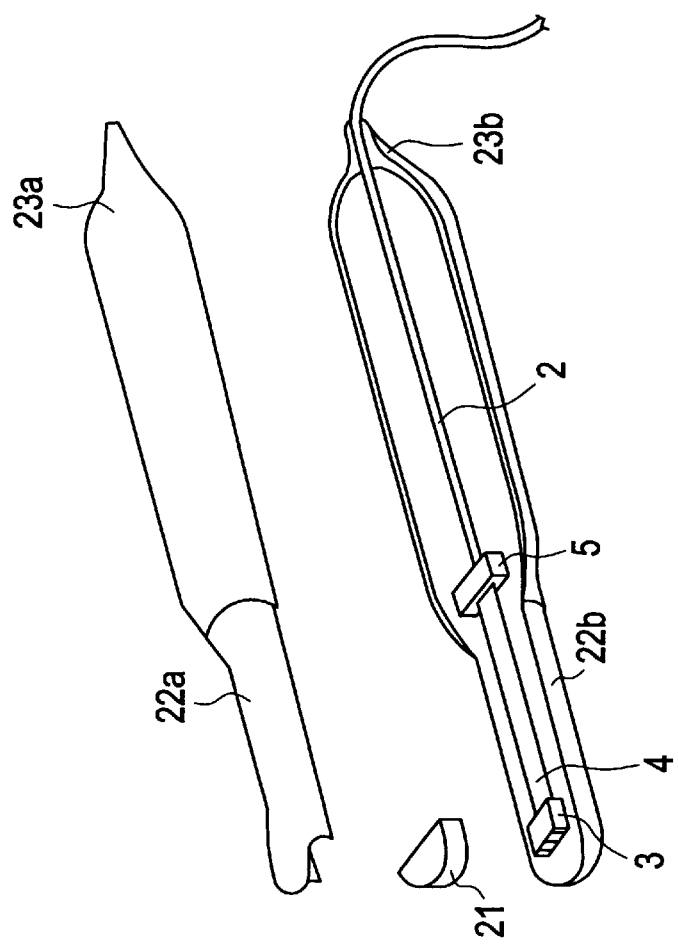
FIG. 6 is an exploded view of the ultrasonic probe 20 shown in FIG. 4.

Process of making the ultrasonic probe 20 will next be described with reference to FIG. 6. FIG. 6 is an exploded view of the ultrasonic probe 20. The ultrasonic probe 20 is made by separately forming the ultrasonic lens portion 21, a case member 22a, and a case member 22b, and combining them.

The case members 22a and 22b are made of a hard resin, and are provided with a bushing member 23a and a bushing member 23b, respectively, of a rubbery material on the surface of the hard resin. The bushing members 23a and 23b are formed using two-color molding so that they cover the surface of the case members 22a and 22b corresponding to the grip portion 24.

The procedure of making the ultrasonic probe 20 involves separately forming the ultrasonic lens portion 21, case member 22a and case member 22b first. Next, the ultrasonic element 3, broad cable 4, connector 5, and connection cable 2 are fitted into the case member 22b. Then, the ultrasonic lens portion 21, case member 22a and case member 22b are assembled, and the ultrasonic probe 20 can be thus obtained.

As described above, since the bushing portion 23 and the case 22 are formed using two-color molding in the ultrasonic probe 20 in accordance with Embodiment 2, the number of molds for use in manufacture is reduced and the number of assembling steps is reduced, thus reducing the cost of manufacture.

Moreover, since the bushing portion 23 is made of a rubbery material, it fully achieves its function as the cable protection portion, and at the same time, slipping is prevented and grippability is improved in the grip portion 24.

While the connection cable 2 and the broad cable 4 are connected to each other via the connector 5 in this embodiment, a configuration in which the connection cable 2 is soldered directly to the broad cable 4 without the connector 5 is possible.

Embodiment 3.

An ultrasonic probe in accordance with Embodiment 3 will now be described. While the case 12, ultrasonic lens portion 11 and bushing portion 13 are formed by integral molding in the ultrasonic probe 10 in accordance with Embodiment 1, an ultrasonic probe 30 presented in Embodiment 3 has an ultrasonic lens portion and a busing portion integrally molded beforehand, and a case is formed on their surface. The remainder of the configuration is similar to the ultrasonic probe 10 described in Embodiment 1, and similar components are designated by similar symbols.

Figure 7:
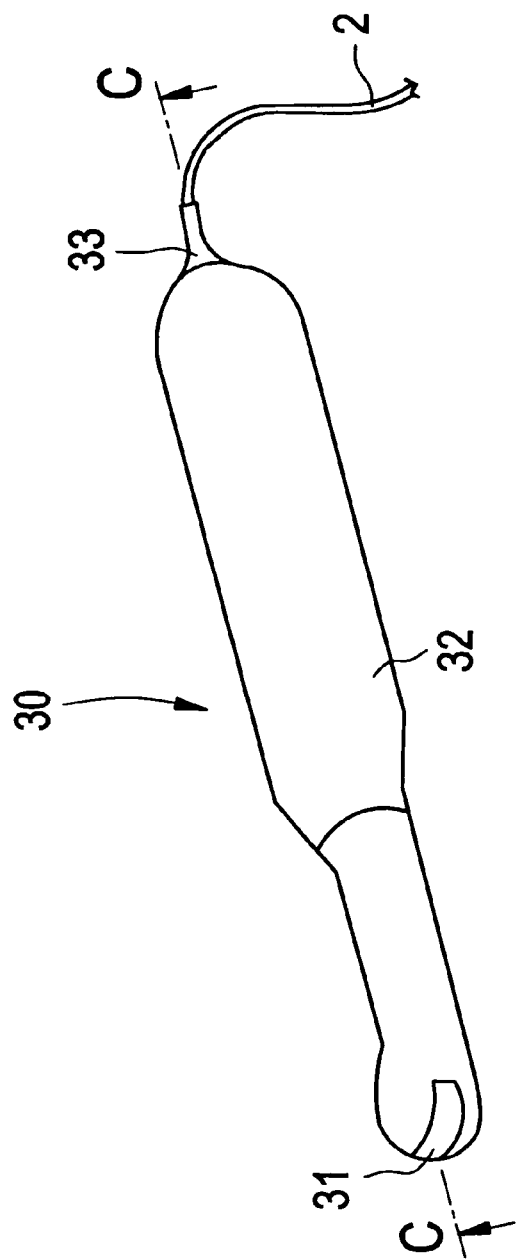
FIG. 7 is a perspective view showing the general configuration of an ultrasonic probe 30 that is Embodiment 3 of the present invention.
Figure 8:
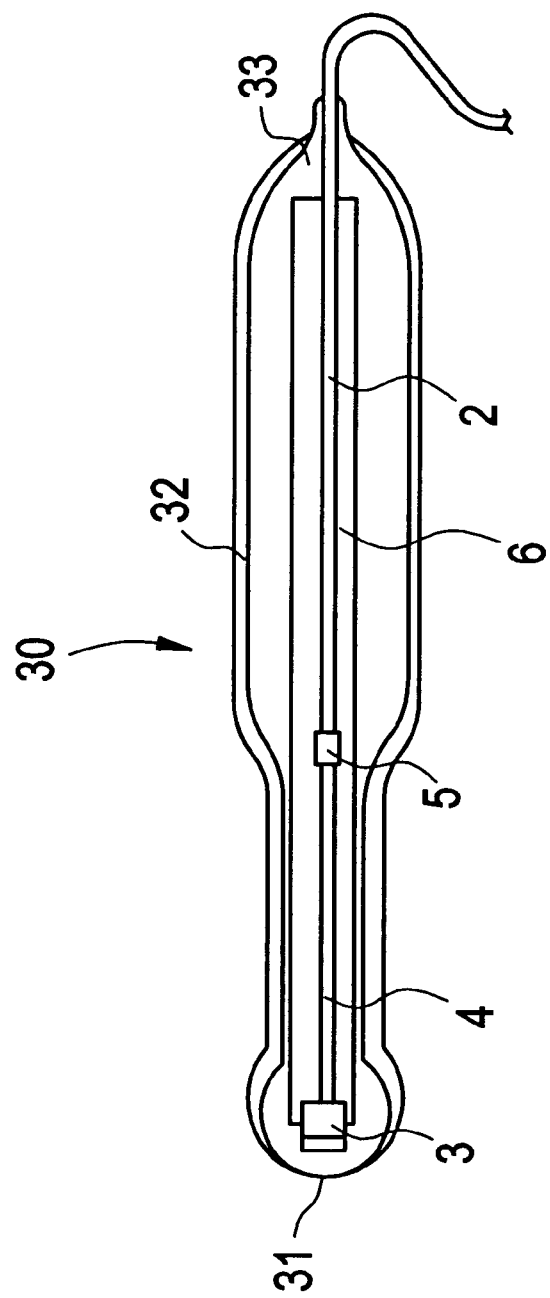
FIG. 8 is a cross-sectional view of the ultrasonic probe 30 shown in FIG. 7 taken along line C—C.

FIG. 7 is a perspective view showing the general configuration of the ultrasonic probe 30 that is Embodiment 3 of the present invention. FIG. 8 is a cross-sectional view of the ultrasonic probe 30 shown in FIG. 7 taken along line C—C. In FIGS. 7 and 8, the ultrasonic probe 30 comprises a silicon material that is integrally molded within a case 32 to form an ultrasonic lens portion 31 and a bushing portion 33. The silicon material has therein an ultrasonic element 3, a broad cable 4, a connector 5, and a fixing member 6.

The ultrasonic element 3 is fitted in the fixing member 6, and disposed near the tip portion of the silicon material. The broad cable 4 connected with the ultrasonic element 3 is connected to a connection cable 2 via the connector 5, and the connection cable 2 is connected to an ultrasonic imaging apparatus (not shown). It should be noted that the broad cable 4, connector 5 and connection cable 2 are fitted in the fixing member 6 and are fixed.

The silicon material forms the ultrasonic lens portion 31 near the ultrasonic element 3. The silicon material also forms the bushing portion 33 at a pass-through portion through which the connection cable 2 passes into the silicon material. The bushing portion 33 serves as a cable protection portion for preventing breakage of the connection cable 2 by limiting flexure of the connection cable 2 at the pass-through portion. The case 32 forms a grip portion 34 that can be gripped by the operator and that covers the surface of the silicon material with the ultrasonic lens portion 31 and bushing portion 33 exposed.

The ultrasonic element 3 is supplied with electric power from the broad cable 4, and generates ultrasound. The generated ultrasound is focused by the ultrasonic lens portion 31, and the subject to be imaged is illuminated with the focused ultrasound. The ultrasonic element 3 also receives reflection waves that are ultrasound reflected by the subject to be imaged, converts the received waves into electric signals, and outputs them to the broad cable 4. The broad cable 4 transmits the electric signals output by the ultrasonic element 3 to the ultrasonic imaging apparatus (not shown) via the connector 5 and connection cable 2. The ultrasonic imaging apparatus produces an image of the imaged subject based on the electric signals received from the connection cable 2.

In performing imaging, the operator grips the grip portion 34 and puts the ultrasonic lens portion 31 against a desired portion in the subject to be imaged to conduct imaging. At that time, a solvent for ultrasonic examination may be applied to the subject to be imaged. The solvent for ultrasonic examination is a gel-type solvent that has an acoustic impedance similar to that of the human body and prevents attenuation of ultrasound. By applying such a solvent, multiple reflection can be suppressed and noise can be prevented. The tip portion of the ultrasonic probe 30 may be inserted into the body cavity, i.e., into the esophagus, intestine, vagina, anus or the like, to acquire information on the interior of the living body.

In making the ultrasonic probe 30, the ultrasonic element 3, broad cable 4, connector 5, and connection cable 2 are first fitted in the fixing member 6. Insert molding is next used to mold the silicon material surrounding the fixing member 6 to form the ultrasonic lens portion 31 and the bushing portion 33. Next, the case 32 is insert-molded using a hard resin, and the ultrasonic probe 30 can thus be obtained.

As described above, since the ultrasonic lens portion 31 and the bushing portion 13 are integrally molded of the same material, and the case 32 is formed by insert molding in the ultrasonic probe 30 in accordance with Embodiment 3, the number of members is reduced, the number of assembling steps is reduced, and reduction in the cost of manufacture can thus be achieved.

Moreover, since the case 32 is separately formed using insert molding of a hard resin, gaps and seams are eliminated in the appearance of the ultrasonic probe 30, improving aesthetics, and at the same time, the strength of the ultrasonic probe 30 is improved.

While the connection cable 2 and the broad cable 4 are connected to each other via the connector 5 in this embodiment, a configuration in which the connection cable 2 is soldered directly to the broad cable 4 without the connector 5 is possible.

Embodiment 4.

An ultrasonic probe in accordance with Embodiment 4 will now be described. While the case, ultrasonic lens portion and bushing portion are formed by integral molding in the ultrasonic probe 10 in accordance with Embodiment 1 as described above, an ultrasonic probe 40 in this embodiment has a case and an ultrasonic lens portion integrally molded, and a bushing portion is separately molded. The remainder of the configuration is similar to the ultrasonic probe 10 described in Embodiment 1, and similar components are designated by similar symbols.

Figure 9:
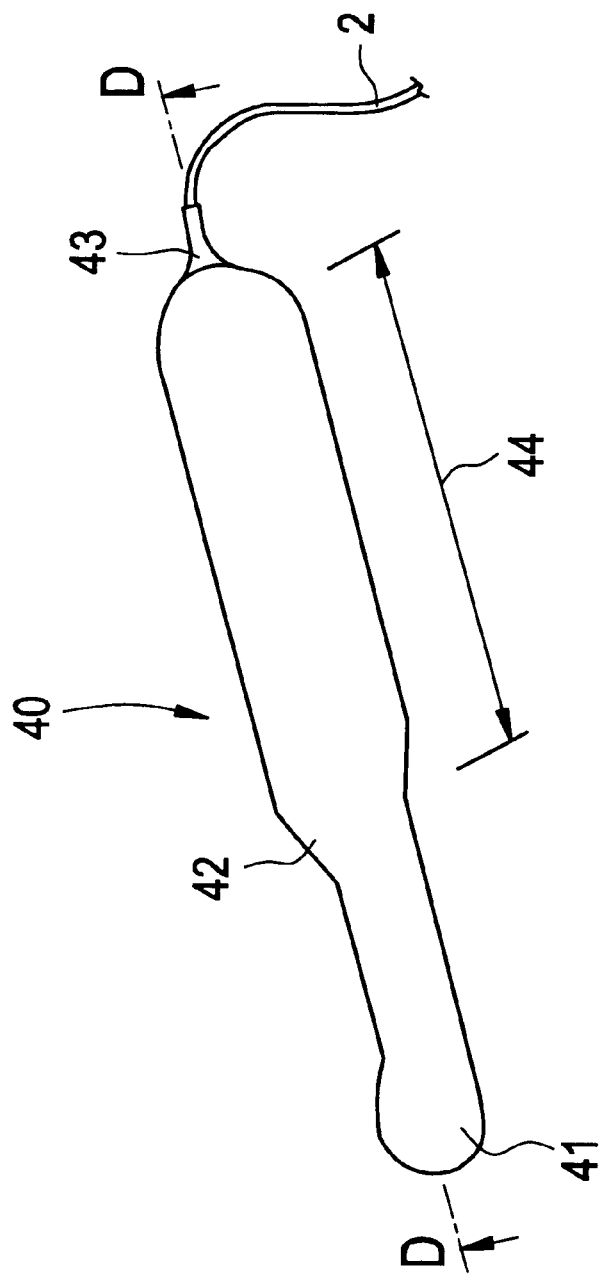
FIG. 9 is a perspective view showing the general configuration of an ultrasonic probe 40 that is Embodiment 4 of the present invention.
Figure 10:
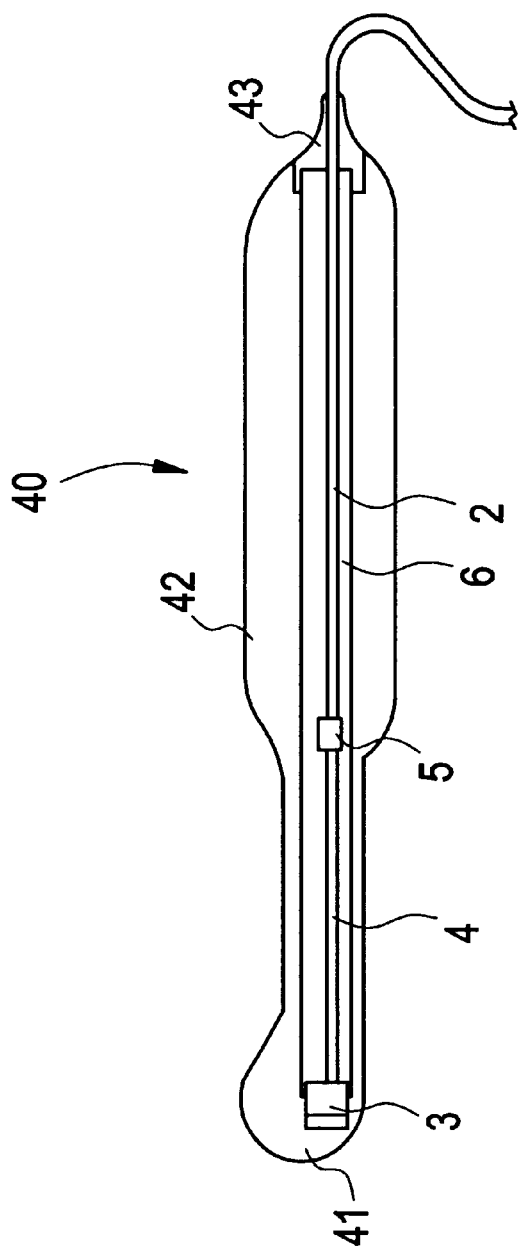
FIG. 10 is a cross-sectional view of the ultrasonic probe 40 shown in FIG. 9 taken along line D—D.

FIG. 9 is a perspective view showing the general configuration of the ultrasonic probe 40 that is Embodiment 4 of the present invention. FIG. 10 is a cross-sectional view of the ultrasonic probe 40 shown in FIG. 9 taken along line D—D. In FIGS. 9 and 10, the ultrasonic probe 40 has therein an ultrasonic element 3, a broad cable 4, a connector 5, and a fixing member 6. The ultrasonic element 3 is fitted in the fixing member 6, and disposed near the tip portion of a case 42. The broad cable 4 connected with the ultrasonic element 3 is connected to a connection cable 2 via the connector 5, and the connection cable 2 is connected to an ultrasonic imaging apparatus (not shown). It should be noted that the broad cable 4, connector 5 and connection cable 2 are fitted in the fixing member 6 and are fixed.

The case 42 forms an ultrasonic lens portion 41 near the ultrasonic element 3. The ultrasonic probe 40 comprises a bushing portion 43 at a pass-through portion through which the connection cable 2 passes into the case 42. The bushing portion 43 is made of a rubbery material, and serves as a cable protection portion for preventing breakage of the connection cable 2 by limiting flexure of the connection cable 2 at the pass-through portion. The case 42 also forms a grip portion 44 that can be gripped by the operator.

The ultrasonic element 3 is supplied with electric power from the broad cable 4, and generates ultrasound. The generated ultrasound is focused by an ultrasonic lens portion 41, and the subject to be imaged is illuminated with the focused ultrasound. The ultrasonic element 3 also receives reflection waves that are ultrasound reflected by the subject to be imaged, converts the received waves into electric signals, and outputs them to the broad cable 4. The broad cable 4 transmits the electric signals output by the ultrasonic element 3 to the ultrasonic imaging apparatus (not shown) via the connector 5 and connection cable 2. The ultrasonic imaging apparatus produces an image of the imaged subject based on the electric signals received from the connection cable 2.

In performing imaging, the operator grips the grip portion 44 and puts the ultrasonic lens portion 41 against a desired portion in the subject to be imaged to conduct imaging. At that time, a solvent for ultrasonic examination may be applied to the subject to be imaged. The tip portion of the ultrasonic probe 40 may be inserted into the body cavity, i.e., into the esophagus, intestine, vagina, anus or the like, to acquire information on the interior of the living body.

In making the ultrasonic probe 40, the ultrasonic element 3, broad cable 4, connector 5, and connection cable are first fitted in the fixing member 6. Next, the bushing portion 43 is formed in the fixing member 6. The fixing member 6 is then positioned in the interior of a mold having a cavity corresponding to the case 42; and by injecting into the cavity a silicon resin that will serve as the ultrasonic lens, the case 42 and the ultrasonic lens portion 41 can be integrally molded.

As described above, since the ultrasonic lens portion 41 is formed simultaneously with the case 42 during integral molding of the case 42 in the ultrasonic probe 40 in accordance with Embodiment 4, the case 42 and ultrasonic lens portion 41 can be made using a single mold. Thus, the number of members is reduced, the number of assembling steps is reduced, and reduction in the cost of manufacture can thus be achieved.

Moreover, since the ultrasonic lens portion 41 and the case 42 are integrally molded by integral molding of the silicon material that serves as the ultrasonic lens, slipping is prevented and grippability is improved in the grip portion 44. Furthermore, by integral molding the case 42, gaps and seams are eliminated in the appearance of the ultrasonic probe 40, improving aesthetics.

While the connection cable 2 and the broad cable 4 are connected to each other via the connector 5 in this embodiment, a configuration in which the connection cable 2 is soldered directly to the broad cable 4 without the connector 5 is possible.

Embodiment 5.

An ultrasonic probe in accordance with Embodiment 5 will now be described. While the case, ultrasonic lens portion and bushing portion are formed by integral molding in the ultrasonic probe 10 in accordance with Embodiment 1 as described above, an ultrasonic probe 50 presented in Embodiment 5 has a case and bushing portion integrally molded, and an ultrasonic lens portion is separately molded. The remainder of the configuration is similar to the ultrasonic probe 10 described in Embodiment 1, and similar components are designated by similar symbols.

Figure 11:
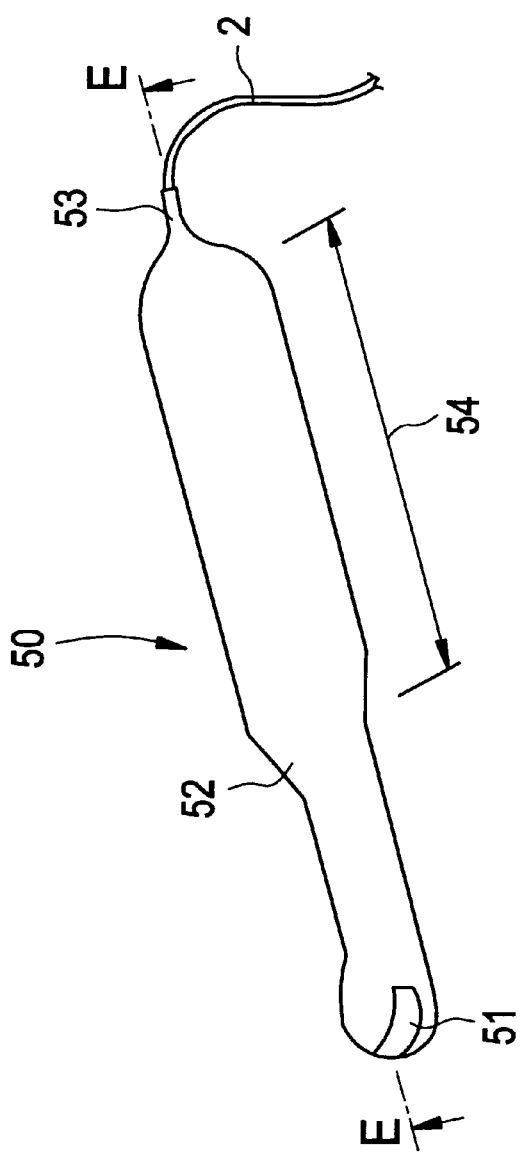
FIG. 11 is a perspective view showing the general configuration of an ultrasonic probe 50 that is Embodiment 5 of the present invention.
Figure 12:
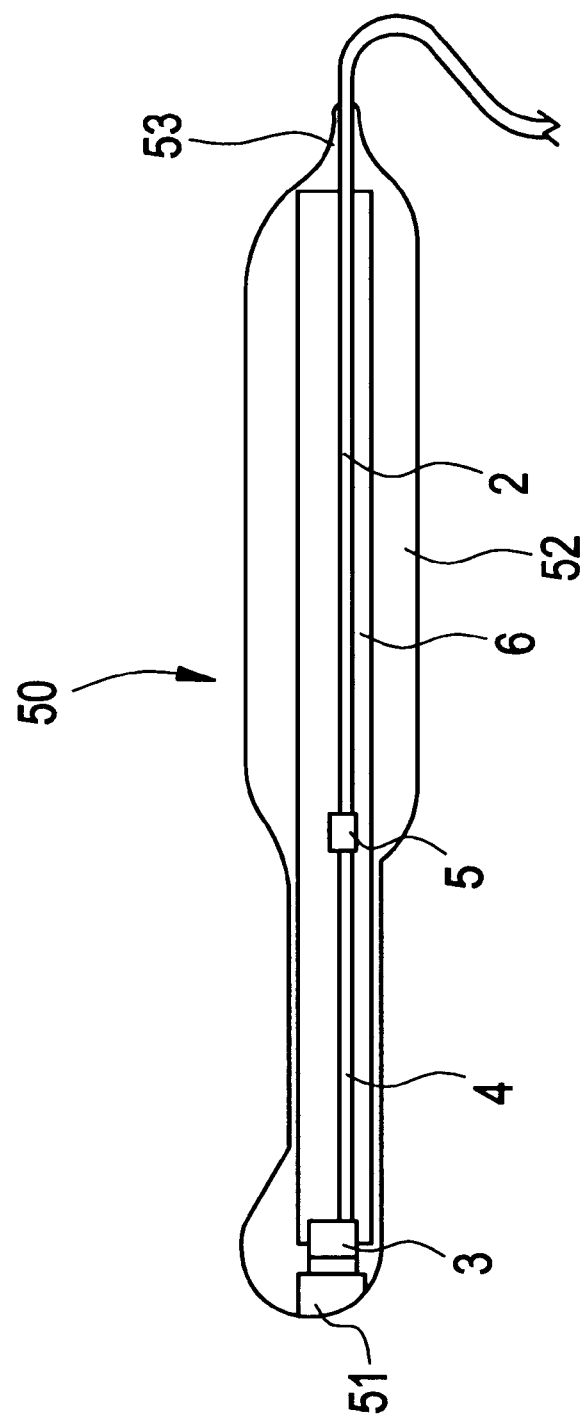
FIG. 12 is a cross-sectional view of the ultrasonic probe 50 shown in FIG. 11 taken along line E—E.

FIG. 11 is a perspective view showing the general configuration of the ultrasonic probe 50 that is Embodiment 5 of the present invention. FIG. 12 is a cross-sectional view of the ultrasonic probe 50 shown in FIG. 11 taken along line E—E. In FIGS. 11 and 12, the ultrasonic probe 50 comprises an ultrasonic lens portion 51 at the tip portion of a case 52, and an ultrasonic element 3 inside the ultrasonic lens portion 51. A broad cable 4 connected with the ultrasonic element 3 is connected to a connection cable 2 via the connector 5, and the connection cable 2 is connected to an ultrasonic imaging apparatus (not shown). The ultrasonic lens portion 51, ultrasonic element 3, broad cable 4, connector 5 and connection cable 2 are fitted in a fixing member 6 and are fixed.

The case 52 forms a bushing portion 53 at a pass-through portion through which the connection cable 2 passes into the case 52. The bushing portion 53 serves as a cable protection portion for preventing breakage of the connection cable 2 by limiting flexure of the connection cable 2 at the pass-through portion. The case 52 has the ultrasonic lens portion 51 exposed near the ultrasonic element 3. The case 52 also forms a grip portion 54 that can be gripped by the operator.

The ultrasonic element 3 is supplied with electric power from the broad cable 4, and generates ultrasound. The generated ultrasound is focused by the ultrasonic lens portion 51, and the subject to be imaged is illuminated with the focused ultrasound. The ultrasonic element 3 also receives reflection waves that are ultrasound reflected by the subject to be imaged, converts the received waves into electric signals, and outputs them to the broad cable 4. The broad cable 4 transmits the electric signals output by the ultrasonic element 3 to the ultrasonic imaging apparatus (not shown) via the connector 5 and connection cable 2. The ultrasonic imaging apparatus produces an image of the imaged subject based on the electric signals received from the connection cable 2.

In performing imaging, the operator grips the grip portion 54 and puts the ultrasonic lens portion 51 against a desired portion in the subject to be imaged to conduct imaging. At that time, a solvent for ultrasonic examination may be applied to the subject to be imaged. The tip portion of the ultrasonic probe 50 may be inserted into the body cavity, i.e., into the esophagus, intestine, vagina, anus or the like, to acquire information on the interior of the living body.

In making the ultrasonic probe 50, the ultrasonic lens portion 51, ultrasonic element 3, broad cable 4, connector 5, and connection cable are first fitted in the fixing member 6. The fixing member 6 is then positioned in the interior of a mold having a cavity corresponding to the case 52; and the case 52 and bushing portion 53 both made of a rubbery material are integrally molded on the surface of the fixing member 6 by insert molding.

As described above, since the bushing portion 53 is formed simultaneously with the case 52 during integral molding of the case 52 in the ultrasonic probe 50 in accordance with Embodiment 5, the case 52 and the bushing portion 53 can be made using a single mold. Thus, the number of members is reduced, the number of assembling steps is reduced, and reduction in the cost of manufacture can thus be achieved.

Moreover, since the bushing portion 53 is made of a rubbery material, it fully achieves its function as the cable protection portion, and slipping is prevented and grippability is improved in the grip portion 54.

Furthermore, since the ultrasonic lens portion 51 is a separate member, the function of the ultrasonic lens is not required in the material for the case 52 and bushing portion 53, and a low-cost material can be used, thus further reducing the cost of manufacture. In addition, since the ultrasonic lens portion 51 is fitted in the fixing member 6, positioning of the ultrasonic lens portion 51 relative to the ultrasonic element 3 can be easily achieved.

While the connection cable 2 and the broad cable 4 are connected to each other via the connector 5 in this embodiment, a configuration in which the connection cable 2 is soldered directly to the broad cable 4 without the connector 5 is possible.

Embodiment 6.

An ultrasonic probe in accordance with Embodiment 6 will now be described. The ultrasonic probe had a configuration such that the probe has a tip portion intended for insertion into the body cavity and an ultrasonic element is fitted in the tip portion in Embodiments 1–5 described above, whereas an ultrasonic probe especially suitable for use with the probe put against the surface of the body will be described hereinbelow.

Figure 13:
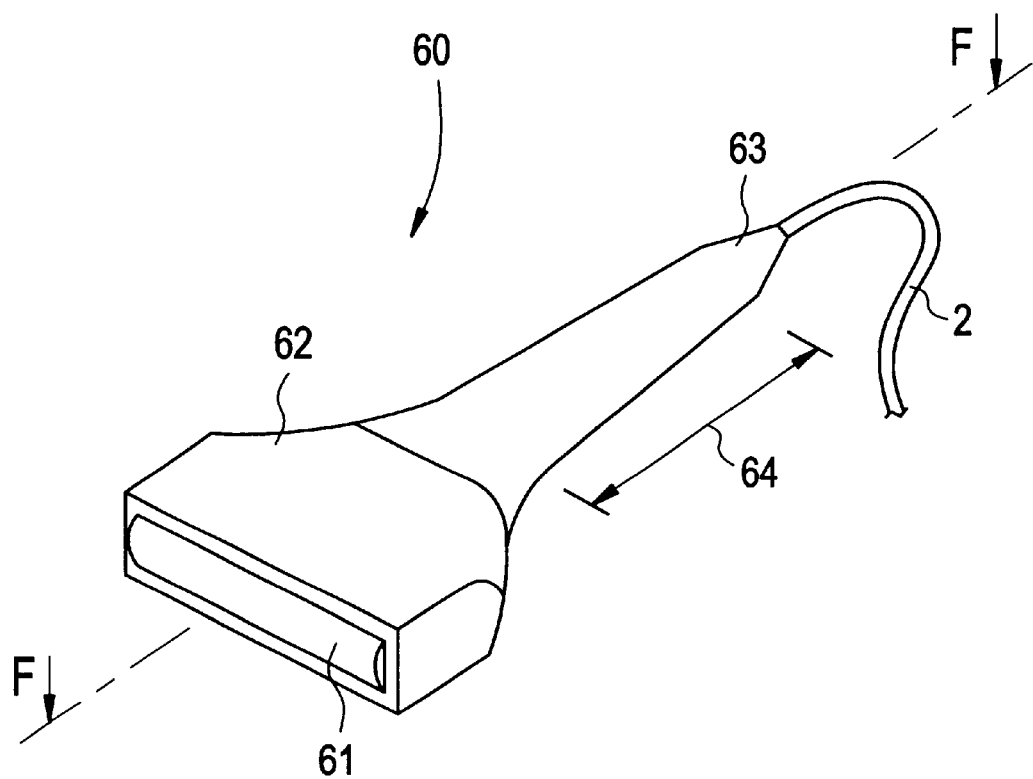
FIG. 13 is a perspective view showing the general configuration of an ultrasonic probe 60 that is Embodiment 6 of the present invention.
Figure 14:
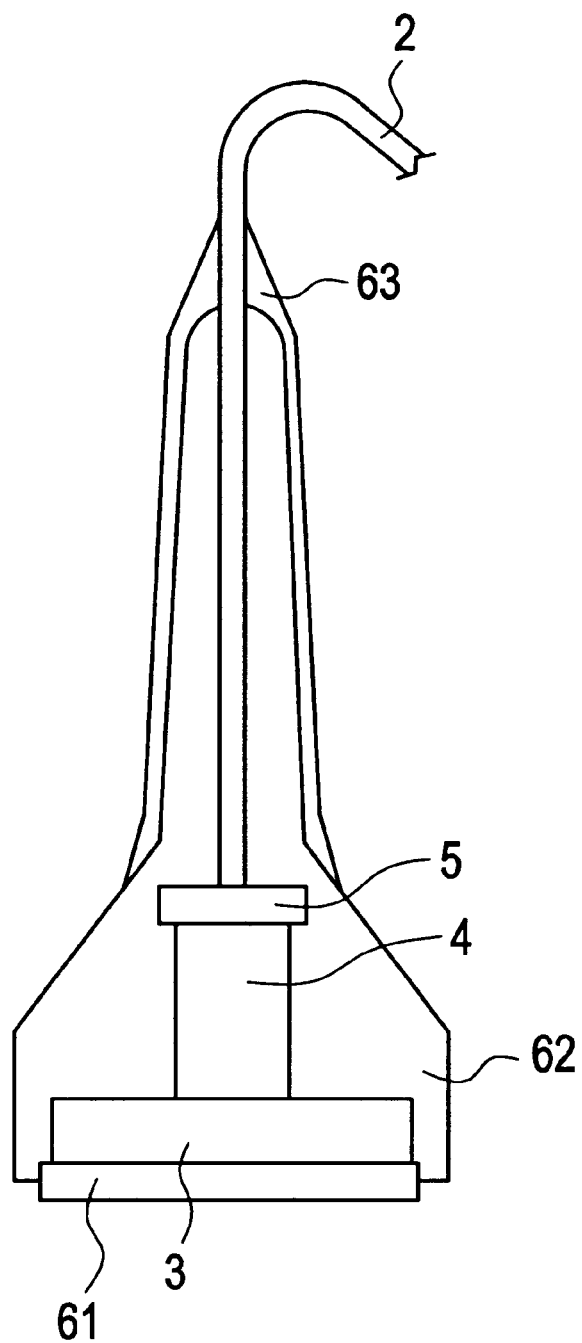
FIG. 14 is a cross-sectional view of the ultrasonic probe 60 shown in FIG. 13 taken along line F—F.
Figure 15:
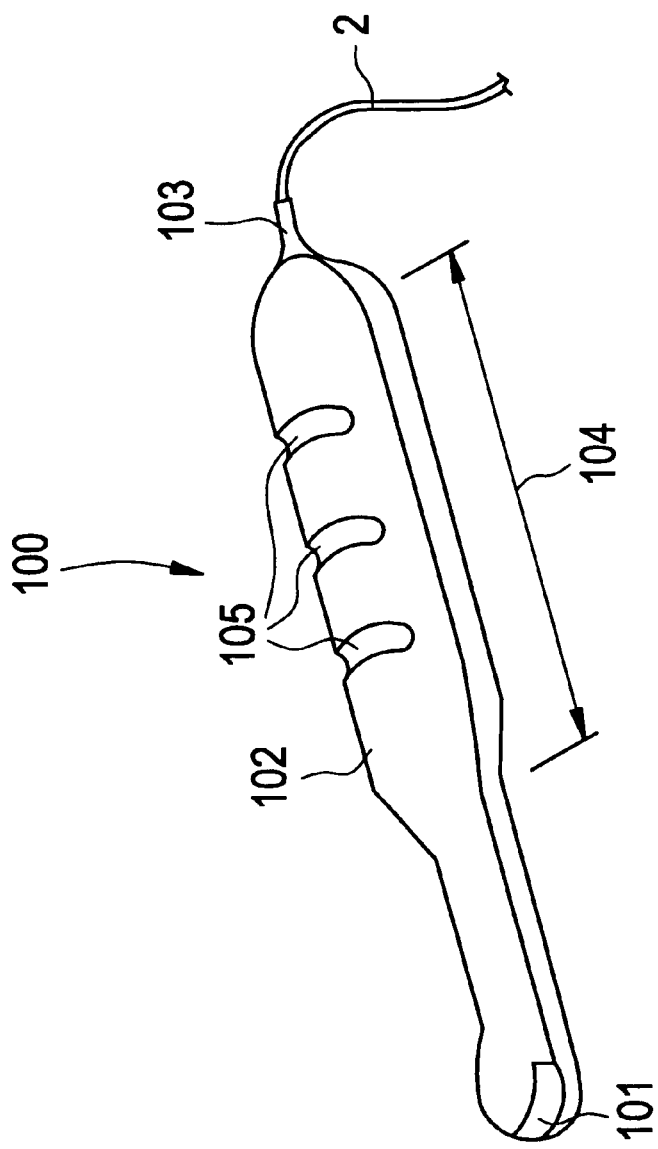
FIG. 15 is a perspective view showing the general configuration of a conventional ultrasonic probe.
Figure 16:
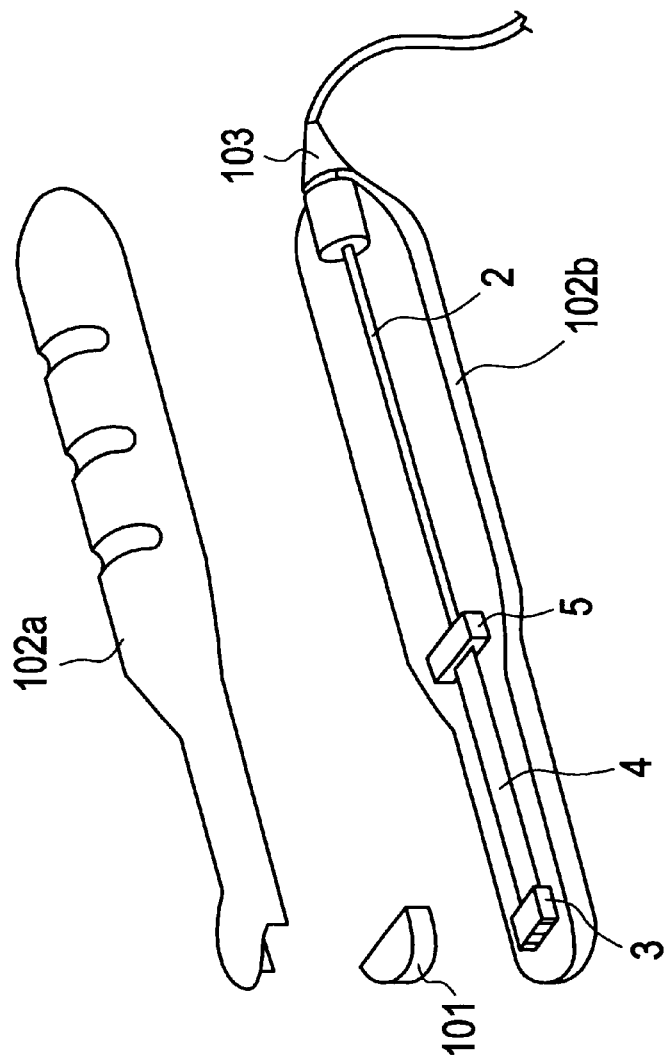
FIG. 16 is an exploded view of the ultrasonic probe shown in FIG. 15.

FIG. 13 is a perspective view showing the general configuration of an ultrasonic probe 60 that is Embodiment 6 of the present invention. FIG. 14 is a cross-sectional view of the ultrasonic probe 60 shown in FIG. 13 taken along line F—F. In FIGS. 13 and 14, the ultrasonic probe 60 comprises an ultrasonic element 3 at one end of a case 62 provided with a grip portion 64, and a connection cable 2 is drawn out from the other end just opposite to the ultrasonic element 3. The end of the case 62 at which the ultrasonic element 3 is disposed is wider than the grip portion 62, and the end is provided with an ultrasonic lens portion 61. The ultrasonic lens portion 61 has a surface extending in a normal direction with respect to the axis of the case 62, and has a shape suitable for being put against the subject to be imaged.

The ultrasonic probe 60 also comprises a bushing portion 63 at a pass-through portion through which the connection cable 2 passes into the case 62. The bushing portion 63 serves as a cable protection portion for preventing breakage of the connection cable 2 by limiting flexure of the connection cable 2 at the pass-through portion. Moreover, the bushing portion 63 covers the grip portion 64, and serves as a slip stopper.

The ultrasonic element 3 is connected to a connection cable 2 via a broad cable 4 and a connector 5, and the connection cable 2 is connected to an ultrasonic imaging apparatus (not shown).

The ultrasonic element 3 is supplied with electric power from the broad cable 4, and generates ultrasound. The generated ultrasound is focused by the ultrasonic lens portion 61, and the subject to be imaged is illuminated with the focused ultrasound. The ultrasonic element 3 also receives reflection waves that are ultrasound reflected by the subject to be imaged, converts the received waves into electric signals, and outputs them to the broad cable 4. The broad cable 4 transmits the electric signals output by the ultrasonic element 3 to the ultrasonic imaging apparatus (not shown) via the connector 5 and connection cable 2. The ultrasonic imaging apparatus produces an image of the imaged subject based on the electric signals received from the connection cable 2.

In performing imaging, the operator grips the grip portion 64, and puts the ultrasonic lens portion 61 against a desired portion in the subject to be imaged to conduct imaging. At that time, a solvent for ultrasonic examination may be applied to the subject to be imaged.

In this embodiment, the bushing portion 63 and the case 62 are formed using two-color molding as in Embodiment 2. By using two-color molding, the number of molds for use in making the ultrasonic probe 60 is reduced and the number of assembling steps is reduced, thus reducing the cost of manufacture.

Moreover, since the bushing portion 63 is made of a rubbery material, it fully achieves its function as the cable protection portion, and at the same time, slipping is prevented and grippability is improved in the grip portion 64.

Although the ultrasonic probe in Embodiment 6 is a modification based on the ultrasonic probe described in Embodiment 2 that is shaped to be especially suitable for imaging with the probe put against the subject to be imaged, the shape in Embodiment 6 may be applied to the ultrasonic probes described in Embodiments 1–5.

While the connection cable 2 and the broad cable 4 are connected to each other via the connector 5 in this embodiment, a configuration in which the connection cable 2 is soldered directly to the broad cable 4 without the connector 5 is possible.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic probe having an ultrasonic element for emitting ultrasound and converting reflection waves of said ultrasound into electric signals, and a cable for supplying electric power to said ultrasonic element and transmitting said electric signals, said ultrasonic probe comprising:

a case for accommodating said ultrasonic element, and provided with a grip portion that can be gripped by an operator;

a cable protection portion provided at a pass-through portion of said cable for limiting flexure of said cable; and an ultrasonic lens for focusing said ultrasound, wherein said ultrasonic lens and said cable protection portion are formed by integral molding, and wherein said case is formed on the surface of said ultrasonic lens and said cable protection portion that are formed by said integral molding.

2. An ultrasonic probe having an ultrasonic element for emitting ultrasound and converting reflection waves of said ultrasound into electric signals, and a cable for supplying electric power to said ultrasonic element and transmitting said electric signals, said ultrasonic probe comprising:

a case for accommodating said ultrasonic element, and provided with a grip portion that can be gripped by an operator;

a cable protection portion provided at a pass-through portion of said cable for limiting flexure of said cable; and an ultrasonic lens for focusing said ultrasound, wherein said case and said cable protection portion are formed by integral molding, and said ultrasonic lens is separately molded.

3. An ultrasonic probe having an ultrasonic element for emitting ultrasound and converting reflection waves of said ultrasound into electric signals, and a cable for supplying electric power to said ultrasonic element and transmitting said electric signals, said ultrasonic probe comprising:

a case for accommodating said ultrasonic element, and provided with a grip portion that can be gripped by an operator;

a cable protection portion provided at a pass-through portion of said cable for limiting flexure of said cable; and an ultrasonic lens for focusing said ultrasound, wherein said ultrasonic lens and said case are formed by integral molding, and said cable protection portion is separately molded.

4. An ultrasonic probe having an ultrasonic element for emitting ultrasound and converting reflection waves of said ultrasound into electric signals, and a cable for supplying electric power to said ultrasonic element and transmitting said electric signals, said ultrasonic probe comprising:

a case for accommodating said ultrasonic element, and provided with a grip portion that can be gripped by an operator;

a cable protection portion provided at a pass-through portion of said cable for limiting flexure of said cable; and an ultrasonic lens for focusing said ultrasound, wherein said case and said ultrasonic lens are separately molded, and a bushing portion is molded over at least a portion of the case.

5. An ultrasonic probe having an ultrasonic element for emitting ultrasound and converting reflection waves of said ultrasound into electric signals, and a cable for supplying electric power to said ultrasonic element and transmitting said electric signals, said ultrasonic probe comprising:

a case for accommodating said ultrasonic element, and provided with a grip portion that can be gripped by an operator;

a cable protection portion provided at a pass-through portion of said cable for limiting flexure of said cable; and an ultrasonic lens for focusing said ultrasound; and a bushing portion molded over at least a portion of the case, wherein said case is fabricated from a material having a first color, and said bushing is fabricated from a material having a second color, said second color different than said first color.

* * * * *